(12) United States Patent
Berger

(10) Patent No.: US 7,806,691 B2
(45) Date of Patent: Oct. 5, 2010

(54) METHOD AND SYSTEM FOR FIXING REMOVABLE DENTURES

(75) Inventor: Uzi Berger, Hod Hasharon (IL)

(73) Assignee: Bio Dental Solution Ltd, Road Town, Tortola (VG)

( * ) Notice: Subject to any disclaimer, the term of this patent is extended or adjusted under 35 U.S.C. 154(b) by 456 days.

(21) Appl. No.: 11/092,985

(22) Filed: Mar. 30, 2005

(65) Prior Publication Data

US 2006/0223029 A1  Oct. 5, 2006

(51) Int. Cl.
A61C 13/00 (2006.01)
A61C 13/02 (2006.01)
A61C 13/28 (2006.01)
A61C 13/12 (2006.01)

(52) U.S. Cl. ............ 433/172; 433/167; 433/168.1; 433/169

(58) Field of Classification Search .......... 433/172–176
See application file for complete search history.

(56) References Cited

U.S. PATENT DOCUMENTS

| 3,277,575 | A | * | 10/1966 | Stasiw .................. 433/198 |
| 4,085,506 | A | | 4/1978 | Lew |
| 4,184,252 | A | | 1/1980 | Krol et al. |
| 4,285,672 | A | * | 8/1981 | Gabriel ................. 433/172 |
| 4,767,328 | A | * | 8/1988 | Branemark ............ 433/168.1 |
| 4,784,608 | A | | 11/1988 | Mays |
| 5,057,017 | A | * | 10/1991 | Sillard ................. 433/172 |
| 5,308,242 | A | * | 5/1994 | McLaughlin et al. ...... 433/114 |
| 5,567,155 | A | | 10/1996 | Hansen |
| 5,674,070 | A | | 10/1997 | Fortin et al. |
| 5,716,214 | A | * | 2/1998 | Lund et al. ............ 433/173 |
| 5,857,853 | A | * | 1/1999 | van Nifterick et al. ..... 433/213 |
| 5,954,506 | A | | 9/1999 | Tanaka |
| 5,997,300 | A | | 12/1999 | Tseng |
| 6,382,975 | B1 | * | 5/2002 | Poirier ................. 433/173 |
| 6,506,052 | B1 | | 1/2003 | Hoffman |
| 6,902,401 | B2 | * | 6/2005 | Jorneus et al. ........... 433/173 |
| 2003/0211444 | A1 | | 11/2003 | Andrews |
| 2004/0038181 | A1 | * | 2/2004 | Fortin ................. 433/173 |

FOREIGN PATENT DOCUMENTS

| EP | 0 305 075 A2 | 3/1989 |
| WO | 00/01318 A1 | 1/2000 |
| WO | 2004075771 A1 | 9/2004 |

OTHER PUBLICATIONS

Branemark, I., et al., "Branemark Novum®: A New Treatment concept for Rehabilitatin of the Edentulous Mandible. Preliminary Results from a Prospective clinical Follow-up Study", vol. 1, No. 1, pp. 1-16, (1999).

* cited by examiner

Primary Examiner—Cris L Rodriguez
Assistant Examiner—Yogesh Patel
(74) Attorney, Agent, or Firm—The Nath Law Group; Derek Richmond

(57) ABSTRACT

A removable denture system comprising a support beam fixedly attached to the individual's alveolar ridge above the mucous membrane by a plurality of dental implants, and a denture generally conforming with the dental parameters of the individual and integrated with a super-structure. The super-structure comprises at least a portion shaped in confirmation with the support beam, and a denture locking arrangement for removably though fixedly articulating the denture to the support beam preventing unintentional disengagement of the denture.

45 Claims, 8 Drawing Sheets

METHOD AND SYSTEM FOR FIXING REMOVABLE DENTURES

FIELD OF THE INVENTION

This invention generally relates to a method and a system for removable attachment of partial/full dentures (removable prosthesis) to an upper and a lower jaw of an individual such that the denture is attachable by a rigid and firm support construction.

BACKGROUND OF THE INVENTION

Partial or complete loss of an individual's natural teeth, either or both at the upper and lower jaw, due to age, accident, diseases or other reasons has some serious effects on an individual both functionally and socially. Lack of teeth poses several serious functional problems such as not being able to chew, speech difficulties, etc. Even more so, a smile with a full set of white teeth is considered something to be desired, i.e. esthetics play an important role.

Utilization of a denture remains a problem. While dentures can be accurately fitted to the alveolar ridge of an individual, it is difficult to retain a denture in position. That is, during normal chewing or talking, the denture has a tendency to ride up out of position on the alveolar ridge, causing speech difficulties, chewing difficulties, and general unsatisfactory use of a denture.

Since the denture is an artificial appliance fitted against living tissue it is best to give that tissue a chance to rest without pressure for some period each day. Many people also have the habit of clenching their teeth when they sleep and this causes even more pressure against tissue and bone in the mouth. It is thus recommended that dentures be removed for some period of the day or night and treat the mouth and gums and clean the dentures.

The denture is a removable dental prosthesis which has artificial teeth embedded in a denture base resembling the gum or gingiva. The denture base provides the support for the prosthesis by resting on the gingiva. The underside of the denture base has a depression receptacle that receives at least a portion of the gingiva so as to provide a snug, reversible fit of the denture onto the gingiva that was adjacent to the lost teeth.

A full denture is used for replacing an entire set of teeth. A full denture would replace the lower set of teeth ("lower denture") or upper set of teeth ("upper denture"). With the full denture, the surface of the depression receptacle base adheres to the appropriate gingiva of the denture wearer through saliva from the wearer's mouth causing a vacuum between the surface of the depression receptacle and the mucus membranes of the gingiva.

A bridge prosthesis is similar to that of a denture prosthesis except the bridge is normally limited to being a partial denture which is non-reversibly cemented or otherwise affixed to the adjacent teeth.

In recent years practice has developed of permanently implanting dental implants (at times referred to as dental fixtures or posts) in the bone structure of the mouth. These permanent dental implants are usually made of titanium which is more acceptable by the body's biological processes and which are locked into position by bone growth. By utilization of the permanently installed implants in the mouth of the individual, the possibility then exists for more readily securing a denture in place either fixedly or removably.

For example, U.S. Pat. No. 5,954,506 discloses a magnetic attachment used for retaining a dental prosthesis, comprising a male part which may be fixed to an abutment and a female part which may be fixed to the dental prosthesis. U.S. Pat. No. 5,997,300 discloses a stake anchored in the base or root of the tooth, and a covering cup is mounted on the denture. An engaging member is placed in the cup chamber, the engaging member being a soft plastic annular member. When a ball head on the stake is engaged therein, the denture is fixed in place, the denture can also be drawn out for removal, so that mounting and removal of the denture at the area missing teeth is convenient.

According to some other particular arrangements, the denture is mounted on an anchor member, which In turn is permanently secured to the individuals gum by means of permanently installed implants. The denture, according to several embodiments is detachable, and according to other embodiments is fixedly attached to said anchor member.

U.S. Pat. No. 4,184,252 is concerned with an overdenture structure and a method for securing it to the residual ridge of a patient. The nerve of at least one healthy tooth is removed and the root canal is filled with dental paste as in a root canal treatment. The crown of the tooth is removed near the gum line and a ferromagnetic bar is embedded in the filled root. Magnetic material is embedded in the overdenture in such position as to be aligned with the ferromagnetic bar at closure points. The dental material surrounding the ferromagnetic bar and the magnetic material embedded in the overdenture are shaped so as to provide contoured mating surfaces with one another. In an alternative embodiment, a root canal treatment is performed on two healthy teeth and bars are embedded in the roots of those teeth. A ferromagnetic rod is connected between the ends of the two bars. Magnetic material is embedded in the overdenture in position to be aligned with the entire length of the ferromagnetic rod. The dental material surrounding the ferromagnetic bars and the magnetic material embedded in the overdenture are shaped so as to provide contoured mating surfaces with one another U.S. Pat. No. 4,784,608 is concerned with an attachment for removably supporting a denture in the mouth of the user in which the user has at least two spaced apart dental implants implanted therein, the attachment including a first basic portion in the form of an anchor member semi-permanently attached to the anchor implant and being curved to generally the shape of the alveolar ridge of the user and having a bar portion extending between the spaced apart dental implants, the anchor member having retention means at the ends thereof such as in the form of a recess at each end. The attachment second basic portion is a denture member which conforms generally to the contour of the anchor member and which is engageable in proximity with the anchor member. The denture member is cast within a denture having simulated gum portions and teeth portions. The denture member has retention means such as integrally formed implants which are removably insertable into the recess in the anchor member, the axis of the implants and the axis of the recesses being inclined toward planes of the anchor member and the denture member. The denture member includes an arm pivotal between a locked and an unlocked position. The arm has a blade portion which engages the anchor member at a point intermediate the retention means so that the arm when in the locked position retains the denture within the mouth of the user, the arm being engagable at its outer end by the fingernail of the user so that it can be pivoted to the unlocked position, allowing the denture to be removed.

U.S. Pat. No. 6,506,052 discloses a system of retrofitting non-dental implant secured dentures with dental implant technology in order to save time and expenses to the denture wearer and to provide a marketing capability that uses the benefits of retrofitted dentures as communicated to denture wearers to convince the denture wearers to receive dental implants. The retrofitting of the said denture comprises of modifying the depression receptacle of the denture base to accept a portion of the exposed part of at least one implant affixed to the denture wearer and to accept a portion of the dental implant securing device. A portion of the dental implant securing device is affixed to the depression receptacle so as to positioned dental implant securing device to reversible attach to at least a portion of the exposed art of at least one implant affixed to the denture wearer when the denture is affixed to the denture wearer.

Still another concept is at times referred to as the Novum™ system and is disclosed in the publication: 'a new treatment concept for rehabilitation of the edentulous mandible. Preliminary results from a prospective clinical follow-up study' [Clinical Implant Dentistry Related Res. 1999;1(1):2-16; by Branemark P I, Engstrand P, Ohrnell L O, Grondahl K, Nilsson P, Hagberg K, Darle C, Lekholm U.]

The present invention provides a system and a method for fixedly though removably supporting a denture in the mouth of an individual, wherein the denture is rigidly secured but in a way so that it is easily and conveniently removed and reinstalled in the individual's mouth, at a sturdy position.

SUMMARY OF THE INVENTION

According to the general aspects of the present invention there is provided a removable denture system wherein the tolerance between a support beam (often referred to in the art as a support bar or a lower bar), fixedly mounted onto the individual's jaw bone and between a super-structure (integrated within the removable denture) is substantially tight, to thereby substantially eliminate any degrees of freedom therebetween, but only for removing of the denture. According to the present invention a denture locking arrangement is provided for preventing unintentional disengagement therebetween, and however substantially not intended to bear any loads. By this it is meant that the locking system is substantially not subjected to mechanical loads such that all loads are born by the support beam, to be dispersed via the implants to the jaw.

The support beam is fixedly applied to the individual's jaw by means of a plurality of fixtures, and the denture is removably fixable over the support beam by means of a superstructure integrated within the denture, such that the denture is sturdily mounted over the support beam.

According to some particular embodiments of the present invention at least an upper portion of the support beam (i.e. that portion which is remote from the jaw bone) has a near to rectangular cross-section, i.e. at least the side surfaces of which are substantially parallel to one another and optionally with a substantially flat top surface, thereby giving rise to a trapezoid section-like shape or, in some particular cases, the top surface is disposed at a right angle to the side surfaces, thereby giving rise to a rectangle section-like shape.

A corresponding cross-section of the super-structure of the denture, practically embraces the support beam, thereby eliminating, or substantially canceling any degrees of freedom therebetween, so as to reduce moments of force developing over dental implants/fixtures and further, such that a person fitted with a denture according to the present invention does not experience unpleasant and insecure feeling of a denture moving in his mouth.

The support beam, according to one specific design, has a near to rectangular cross-section, with an extracting angle (angle of the side walls) of about 4° to 12°, and more likely about 6°.

According to a particular embodiment of the invention the denture locking arrangement comprises inwardly displaceable locking members (i.e. retractable in direction into the individual's mouth) and by specific design, two locking pins laterally retractable inwardly, each extending at or near a side portion of the denture (i.e. extending lateral to the tongue), though medial (frontal) positioning is possible as well, so as to cause minimal interruption and discomfort with the gingiva and tongue.

Readily removable locking of the denture to the support beam is carried out by positive locking i.e. not of the type relying on friction, magnetic force, resilience snap, etc., but rather using locking pin systems or swivel-type lock systems.

According to a first embodiment of the present invention the support structure is an upper bar integrated within the denture, where a bottom surface thereof is fitted for bearing in contact surface over a top surface of the support beam (which in this particular application may be referred to as a lower bar).

According to an other embodiment of the invention, the support structure is a super-structure formed with a support-beam receptacle having a U-like cross-section, conforming with that of at least an upper portion of the support beam for snugly embracing it. In accordance with a modification of the second embodiment the support beam is fixedly fitted, in a non-removable manner, with an upper-bar (giving rise to a uniform support beam of increased height, where the support structure is a super-structure formed with a support-beam receptacle having a U-like cross-section, conforming with that of at least an upper portion of the attached upper-bar, for snugly embracing it, though removably.

According to the first embodiment, the support structure is an upper bar integrated with the personalized denture, i.e. the denture is molded over the upper bar with the locking members being retractable through the upper bar for locking engagement with locking studs projecting vertically from the support beam.

According to the second embodiment of the invention, the personalized denture is integrated with the super-structure, fitted for snugly receiving the support beam, wherein the locking members are retractable through the super-structure for locking engagement directly with suitable bores formed in the support beam. The term snugly as used herein refers to close contact between the super-structure and the support beam, i.e. close/intimate surface contact over substantially the entire surface of the super-structure.

Locking engagement between the locking members and the locking studs is for example by a locking pin fitted for engagement with a busted bore formed in the locking stud or by engagement of said pin with a peripheral grove formed on the locking stud, for arresting the denture to thereby prevent its unintentional removal. Preferably, axial displacement of the locking pins is restricted to thereby prevent their complete retraction.

According to another aspect of the present invention, an individual and personalized support beam is custom manufactured, tailored to the particular anatomy of the individual (namely jaw structure and situation), according to different parameters obtained e.g. by periapical X-ray, panoramic X-ray, CT imaging, study models, etc. of the individual. Accordingly, a personalized kit is prepared, whereby a support beam and dental implants (fixtures) are provided along with a fixture kit comprising positioning templates, pins, drills and mandrels, etc. The support beam is then fixedly attached to the individual's jaw bone over the implants pre-implanted into the jaw (with or without leveling of the alveolar crest, and thereafter a personalized denture is removably attached over the support beam in accordance with any of the embodiments disclosed hereinabove.

The term personalized denture as used hereinabove denotes a denture mimicking the individual's natural teeth and gums (i.e. color, shape, size and matching with the opposite jaw's teeth/denture, etc), typically made of acrylic material (at times with porcelain coating of the artificial teeth formed therein). It is highly desired that each denture according to the present invention be fitted with a skirt (lateral and frontal flange coverage) extending downwards to intimate close contact with the vestibular area, i.e. over the at least a major portion of the gums. The skirt portion simulates and completes the gingival area and offers an aesthetic appearance and to conceal any artificial structure on the one hand, and on the other hand to cover any gaps which normally would exist so as to prevent phonetic disorders (mispronunciation) and saliva and food escape.

Either of the methods above disclosed is suited for both the upper and lower jaws and any locking arrangement is suited for removably though fixedly attaching the denture to the fixed support beam. Furthermore, where the locking members are inwardly retractable pins, there may be formed a narrow bore at the front face of the denture through which an aid may be applied to assist in retraction of the locking pins.

BRIEF DESCRIPTION OF THE DRAWINGS

In order to better understand the invention and to see how it may be carried out in practice, some embodiments will now be described, by way of non-limiting examples only, with reference to the accompanying drawings, in which.

DETAILED DESCRIPTION OF SPECIFIC EMBODIMENTS

Figure 1A:
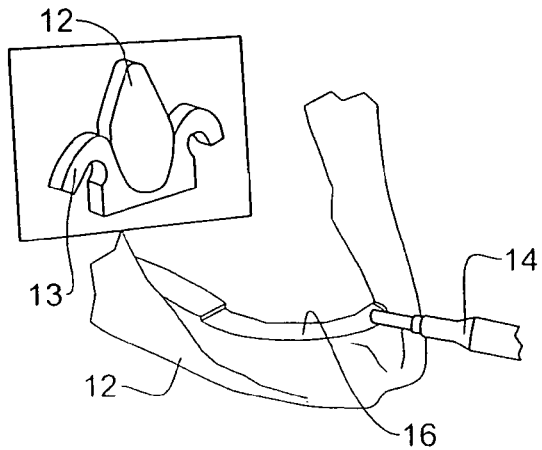
FIGS. 1A through 1F sequentially illustrate steps for installing a prefabricated precision support structure in an individual's lower jaw.
Figure 1B:
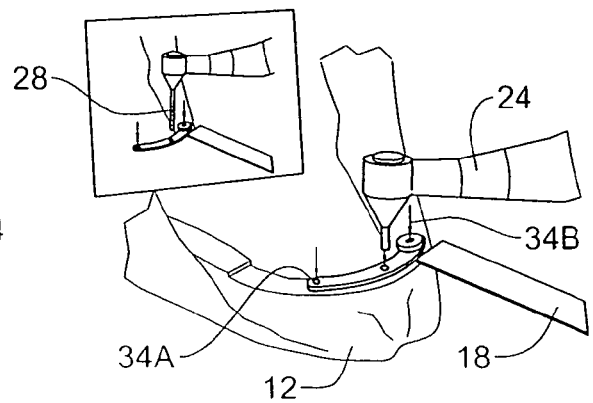
Figure 1C:
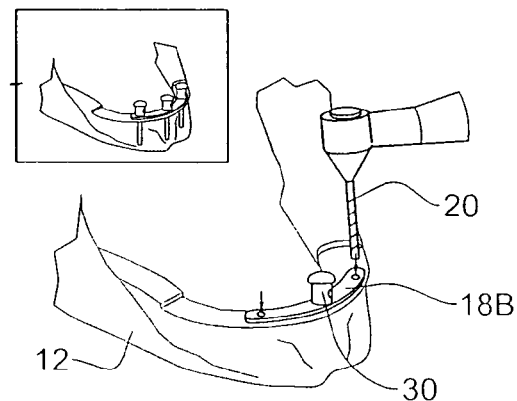
Figure 1D:
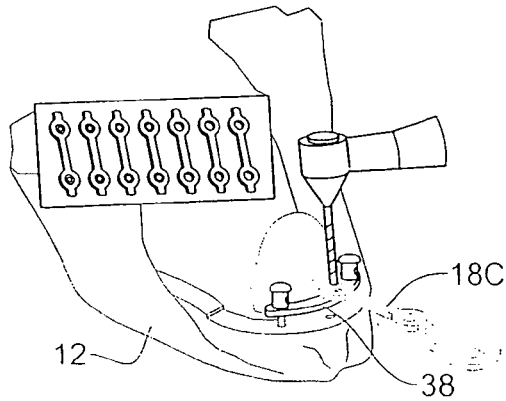
Figure 1E:
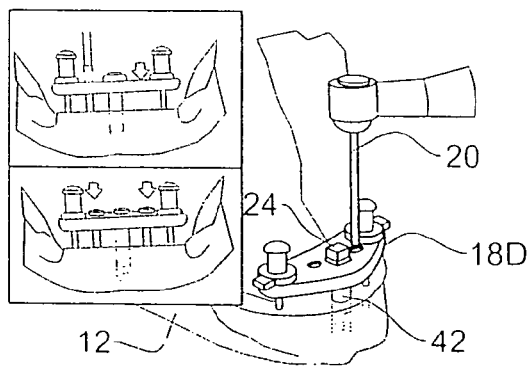
Figure 1F:
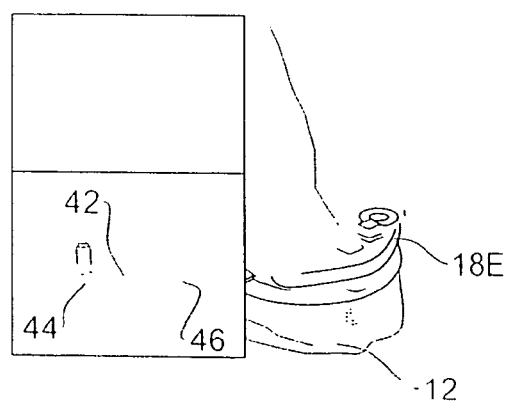
Figure 2A:
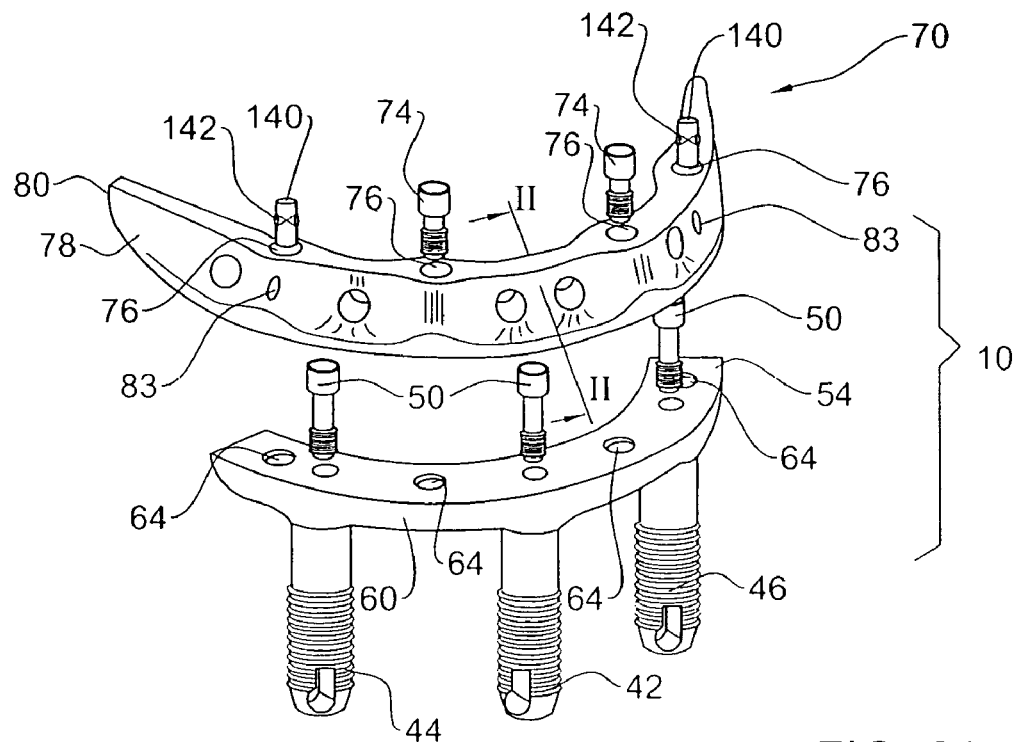
FIG. 2A is an isometric exploded view of the components of the prefabricated precision components.

Attention is first directed to FIGS. 1A through 1F and to 2A and 2B sequentially illustrating a surgical protocol for fitting a rigid denture support beam generally designated 10 (FIG. 2A). After preoperative radiographic examination for determining the characteristics of the jaw bone 12 (low jaw bone in the present example) the individual is anesthetized and a crestal incision is made to expose the jaw bone by incising mucosa 13 (small window in FIG. 1A). Then, the crestal jaw bone in the anterior region is reduced using a rimmer 14 so as to obtain a wide bone platform 16 suitable for accommodating a prefabricated titanium template (18 in FIG. 1D). Several different templates are used during the drilling procedure for gradually increasing the diameter of the preparations made with specially designated drills 20. A first template used is a so-called guide template setting the position of the sites (for the implants) beginning with marking a central fixture position with a standard round bore 24 (FIG. 1B) the marked position was then enlarged using a twist drill (28 in the small window of FIG. 1B). A guide pin 30 (FIG. 1C) is then placed through the guide template 18 and two additional fixture sites 34A and 34B are marked. The evaluation template 18 is then replaced by positioning templates 18B through 18E using suitable drill guides (38 in FIG. 1D) to gradually increase the dimension of the central fixture position and then, as seen in FIG. 1E, a fixture 42 is inserted through the template 18D. The two side sites earlier marked as 34A and 34B are then drilled (FIG. 1E) and their dimension is enlarged (small window in FIG. 1F) to facilitate insertion of two side fixtures 44 and 46.

Then, using a set of titanium screws 50 (FIG. 2B), a lower bar 54 is fixedly secured to the fixtures 42, 44 and 46 in a permanent fashion.

Figure 2B:
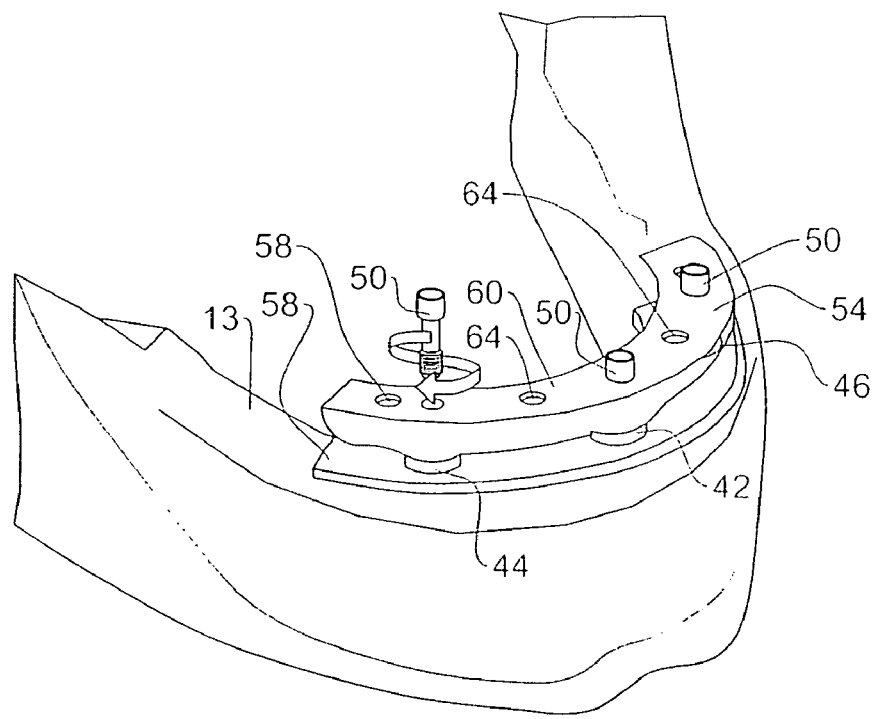
FIG. 2B illustrates a step of permanently fixing a lower bar to the individual's jaw.
Figure 3:
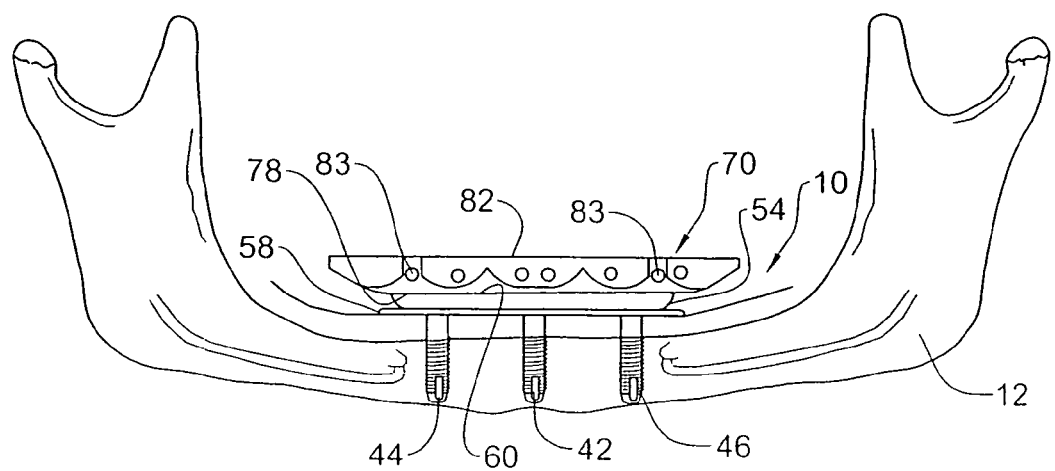
FIG. 3 is a front view of a lower jaw fitted with a prefabricated support system in accordance with a prior art method.

Optionally, a thin silicon support sheet 58 (FIGS. 2B and 3) is placed on the mucosa 13 surrounding the implants 42, 44 and 46 to thereby counteract edema and seal the incision formed during the procedure. It is seen in FIGS. 2A, 2B and 3 that the lower bar 54 has a flat top surface 60 preformed with several threaded bores 64. Placed on the lower bar 54 there is a upper bar generally designated 70 (FIGS. 2A and 3) made of titanium and by means of screws 74 is fixedly attached in abutting engagement to the lower bar 54 such that the lower surface 78 of the upper bar 70 bears flush against the upper surface 60 of the lower bar 54 as can best be seen in FIG. 3, giving rise to a rigidly integrated assembly of the support beam 10. Screws 74 fit into prefabricated bores 76 positioned in coaxial alignment with threaded bores 64 in the lower bar 54.

The upper bar 70 of the support beam 10 is formed with two precise, laterally extending, through-going, apertures 83 (FIGS. 2A and 3) which apertures constitute part of the denture locking mechanism for removably though fixedly mounting a denture thereto, as will become apparent hereinafter.

It is appreciated that the above description follows, at least partially, the so-called Branemark Novum® procedure for example as illustrated in the literature.

Figure 4A:
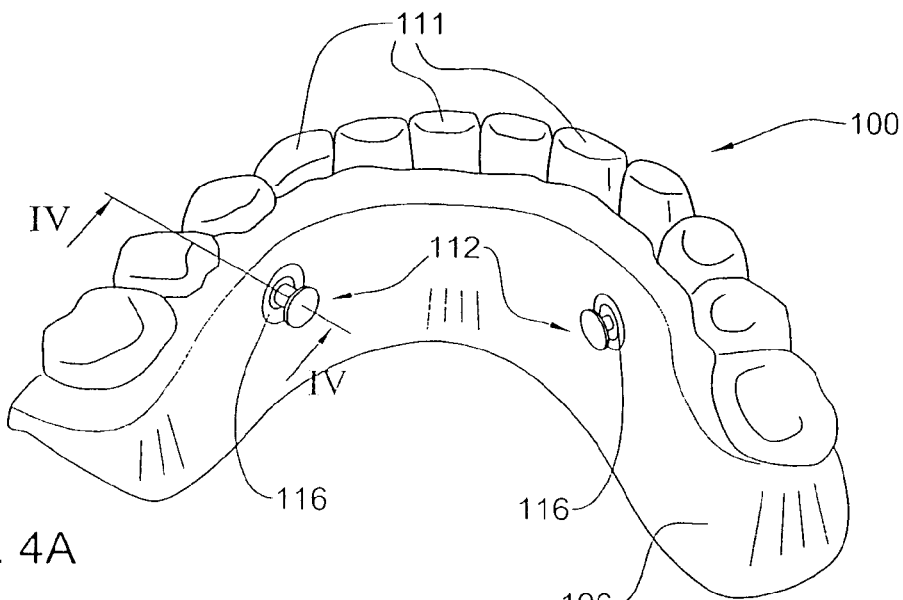
FIG. 4A is a top isometric view from an inside of a denture in accordance with the present invention.
Figure 4B:
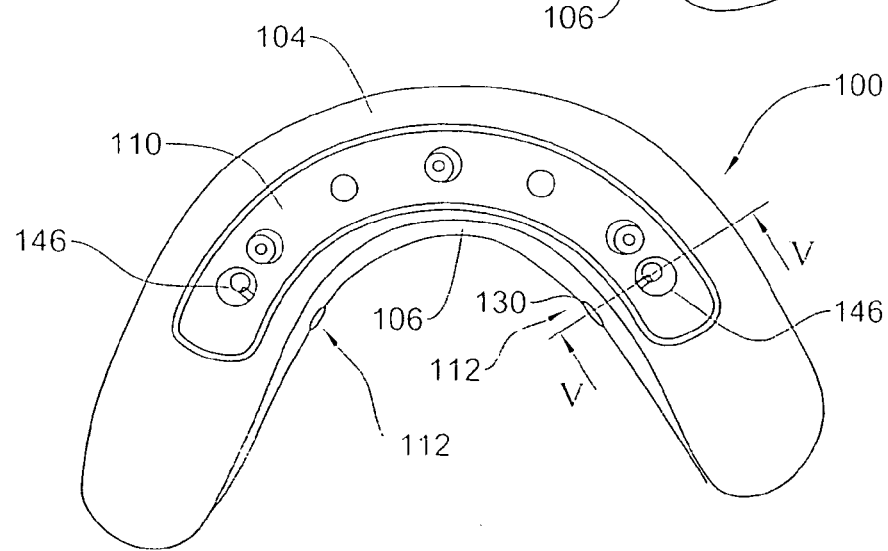
FIG. 4B is a bottom view of the denture as seen in FIG. 4A.

Turning now to FIGS. 4A and 4B there is shown a denture generally designated 100 made of an acrylic material and integrally fitted with a plurality of teeth 111 mimicking the individual's natural teeth as far as shape, size, color, etc. and further comprising a gum mimicking portion (skirt) comprising a front gum portion 104 and a rear gum portion 106, the color and texture of which mimicking the natural appearance of the individual's gum. The skirt (lateral and frontal flange coverage) extends downwards to intimate close contact with the vestibular area, i.e. over the at least a major portion of the gums. The skirt portion simulates and completes the gingival area and offers an aesthetic appearance and to conceal any artificial structure on the one hand, and on the other hand to cover any gaps which normally would exist so as to prevent phonetic disorders (mispronunciation) and saliva and food escape.

Integrated and fixedly received within the denture 100 there is a support structure 110 (FIG. 4B) made of hard material e.g. metal, and having a U-like cross-section conforming with and fitted for snugly receiving and embracing at least the upper portion 80 of a lower bar as will be explained below. The denture 100 is designed to be applied (placed) over a lower bar (not seen in FIG. 4B, identified as 200 in FIGS. 7A and 7B)in a substantially vertical position and removed in the same fashion and further, such that the tolerance between the lower bar 200 and the super structure 110 of the denture 100 is substantially tight to thereby substantially eliminate any degrees of freedom therebetween (apart for allowing removal of the denture as mentioned hereinbefore).

Figure 5A:
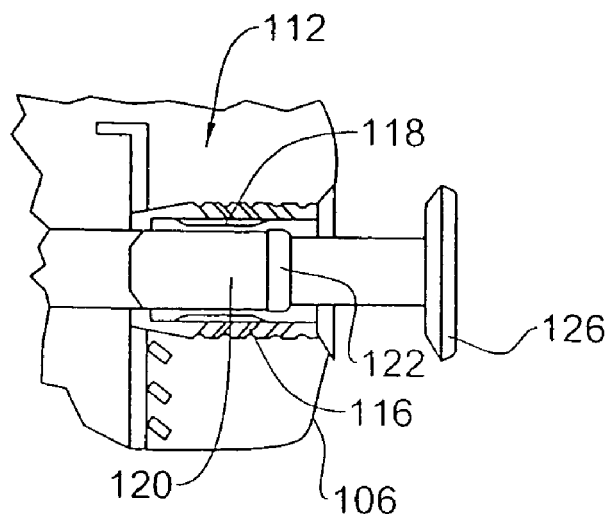
FIGS. 5A and 5B are cross-sectional views along lines IV and V in FIGS. 4A and 4B, respectively, illustrating a locking mechanism in accordance with one particular embodiment in accordance with the present invention.
Figure 5B:
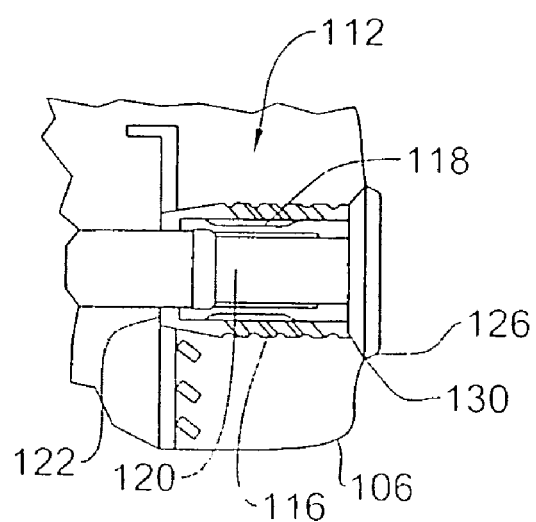

As can further be seen in FIGS. 4A and 4B the denture 100 is fitted with two locks 112 being pin-snapped type locks as can be seen in more detail in FIGS. 5A and 5B. The locks 112 comprise a housing 116 rigidly embedded within the denture 100, said housing being in the form of a fitted with a sleeve 118 typically made of elastomeric or ceramic material and furthermore, comprising a locking pin 120 formed with an annular displacement limiting ring 122 for snapping arrestments by said sleeve 118 between a locked position (FIGS. 4B and 5B respectively) and then an open position (FIGS. 4A and 5A respectively). The locking pin 120 is further fitted with a head 126 which in the locked position is substantially flush with the surface of the inner gum mimicking skirt portion 106 for maximum comfort of the individual though optionaly there exists a small interstice 130 (FIGS. 4B and 5B) to facilitate extracting the locking pin by the individual's fingernail, for example. The arrangement is such that locking pin 120 is fitted for snugly fitting within bores (also referred to as lock-receptacles 220 in FIG. 7B) formed in the lower bar 200.

Whilst one particular locking mechanism has been illustrated, it is appreciated that other forms of locking arrangements may be applied as well, e.g. the so-called swivel-type lock mechanism (not shown).

It is appreciated that the locking mechanism provided substantially does not serve for bearing any loads but rather to prevent unintentional removal of the denture. It is further noticed that the locking mechanism 112 is fitted at an inside surface of the gum mimicking skirt portion lateral to the tongue, so as to cause minimum disturbance and unpleasant feeling, and also to provide an aesthetic appearance. However, at times, one or more locking mechanisms may be fitted at a frontal position (not shown).

In order to facilitate easy extraction of the locking pin, the denture 110 may be fitted with a two through going bores 150 (FIG. 6B) barely noticeable, only upon retracting the individual's lower lip 152, whereby a thin article may be introduced so as to push against the end of the locking pin 120 to facilitate its retraction.

Figure 6A:
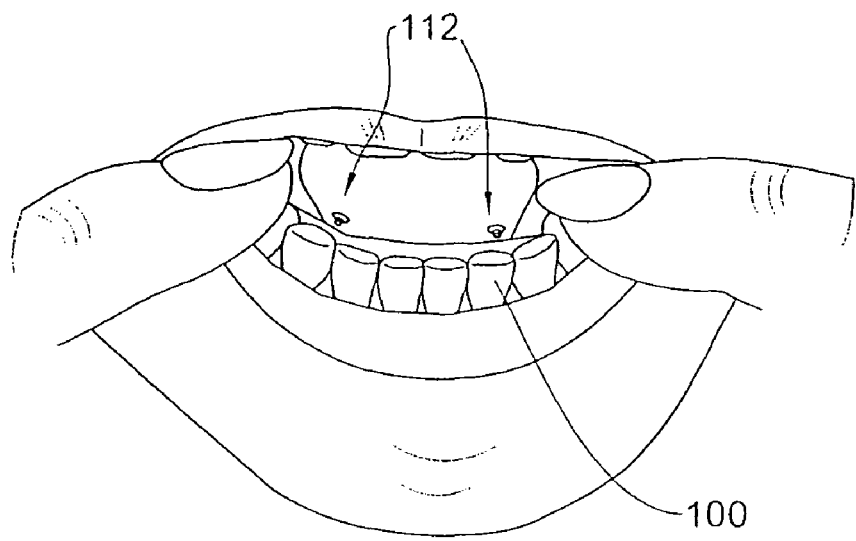
FIG. 6A illustrates positioning and locking of a denture in accordance with an embodiment of the present invention.
Figure 6B:
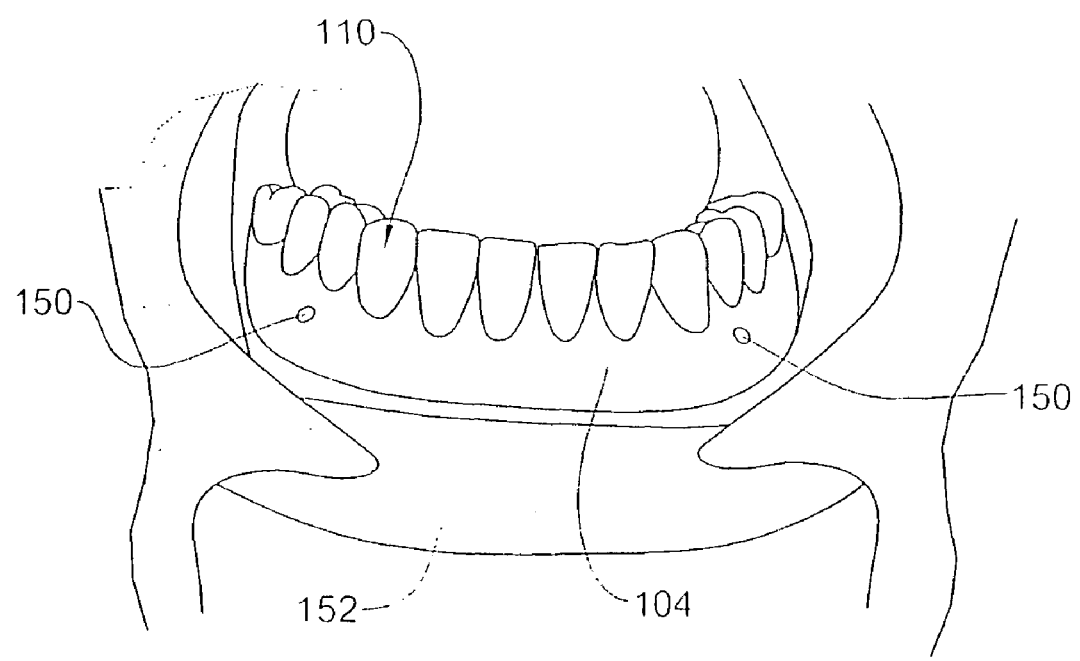
FIG. 6B illustrates a denture in accordance with an embodiment of the present invention fitted in an individual's mouth.

It is further noticed in FIG. 6B that the front skirt of the gum mimicking portion 104 extends downwardly so as to merge with the natural gum of the individual and to substantially conceal all the support structure. This has both an aesthetic meaning and also serves to cover any gaps which normally would exist to thereby prevent phonetic disorders (mispronunciation) and saliva and food escape through such gaps which may obviously cause some unpleasant incidents.

Figure 7A:
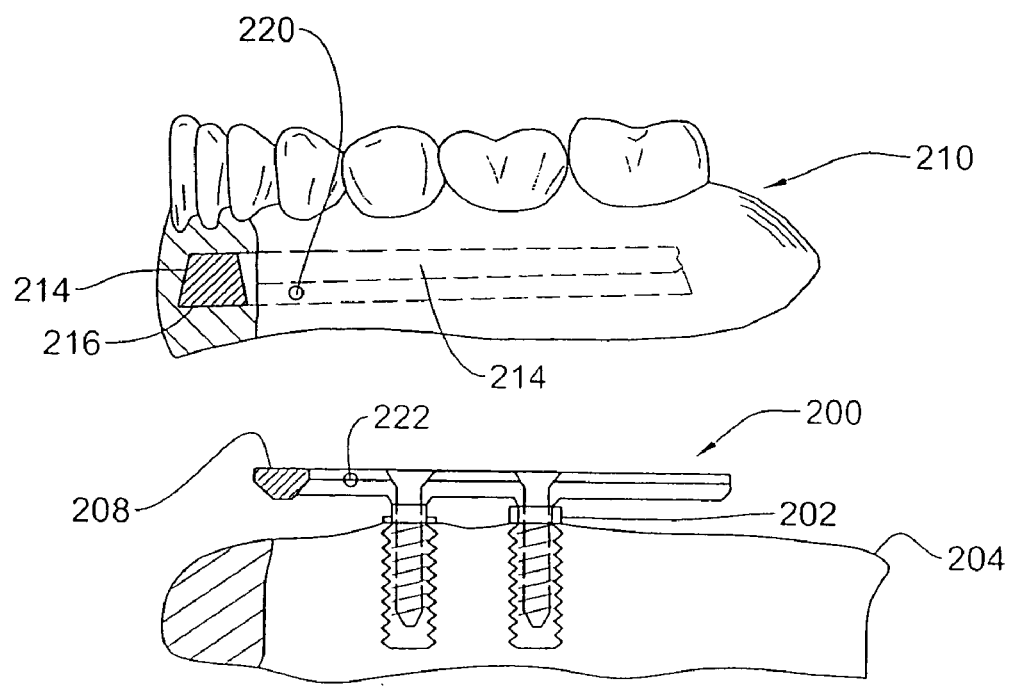
FIG. 7A is a sectioned exploded view of a denture and support beam fixed to a lower jaw, in accordance with another embodiment of the present invention.
Figure 7B:
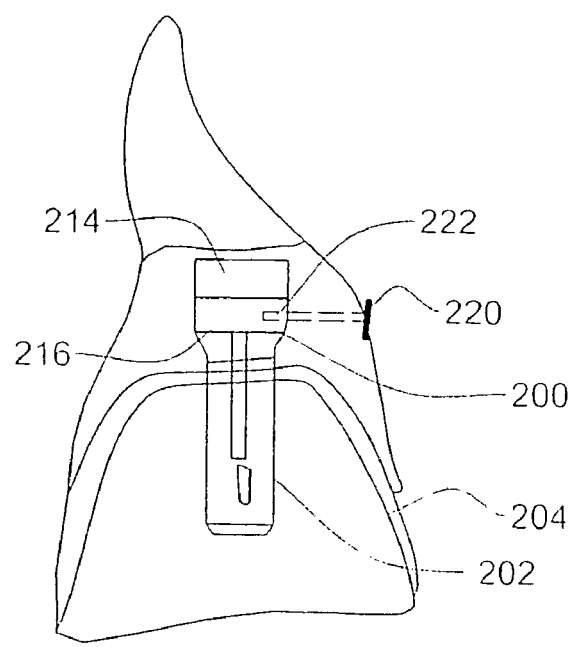
FIG. 7B is a longitudinal section illustrating the denture in accordance with the embodiment of FIG. 7A, removably fitted over an individual's jaw.

With reference now being made to FIGS. 7A and 7B, there is illustrated one embodiment according to the present invention, wherein the support beam 200 is fixed over implants 202 to jaw 204 of an individual, said support beam 200 being in the form of a lower bar, namely having a flat and smooth top surface 208. Integrated and fixedly received within the denture 210 there is a super structure 214. The super structure 214 is made of hard material e.g. metal, and having a smooth and flat bottom surface 216 conforming with and fitted for flush bearing over the top surface 208 of the lower bar 200.

The denture 210 is fitted with a gum-mimicking skirt as discussed in connection with the previous embodiments and further comprises two pin-snap type locks 220 and the lower bar 200 is formed with corresponding lock-receptacles 222 for lockingly arresting the locks 220, e.g. of the type discussed herein above in connection with FIGS. 5A and 5B.

The arrangement in accordance with this embodiment is such that the denture 210 is applied over the lower bar 200 (FIG. 7B) such that the bottom surface 216 of the super structure 214 bears in full contact surface over the top surface 208 of the lower bar 200.

The arrangement is such that the denture 210 is placed over and removed from the support beam 200 in a substantially vertical manner, whereby at the assembled position of FIG. 7B and removed in the same fashion and further, upon locking the locks 220 any degrees of freedom therebetween are substantially eliminated.

This arrangement has significant importance in long-life of the denture support system as minimal moments of inertia develop in the system and in the fixtures. Of further importance is the fact that in an individual fitted with a system in accordance with the present invention substantially does not experience the unpleasant feeling of dentures moving in the mouth.

Figure 8A:
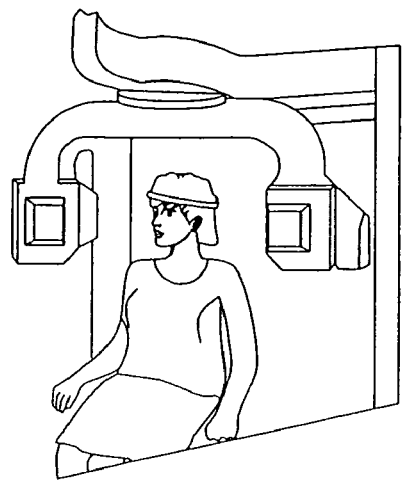
FIGS. 8A through 8H illustrate sequential steps of preparing and fitting a support beam to be used in accordance with a different embodiment of its present invention.
Figure 8B:
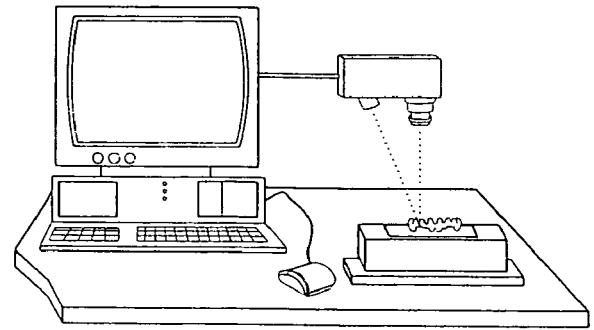
Figure 8C:
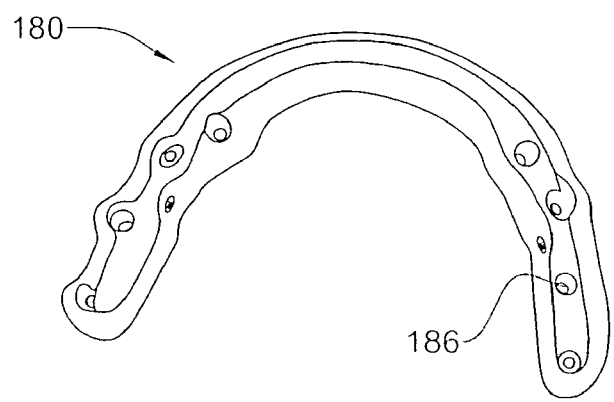
Figure 8D:
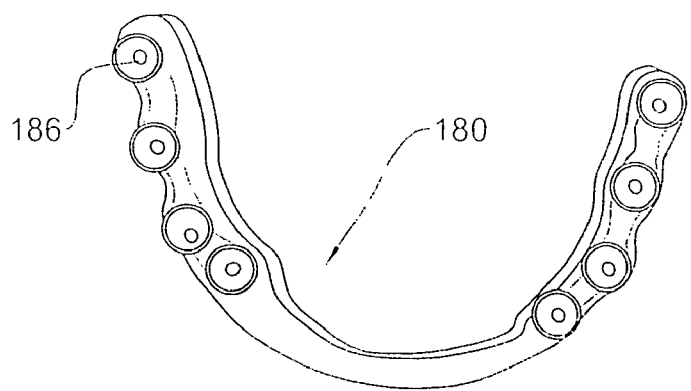
Figure 8E:
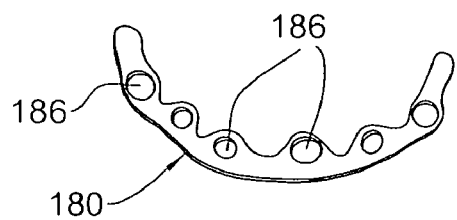
Figure 8F:
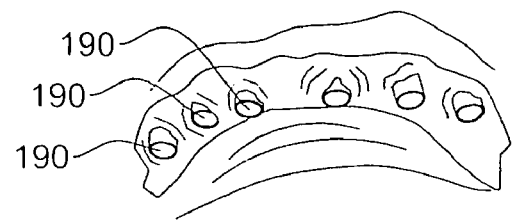
Figure 8G:
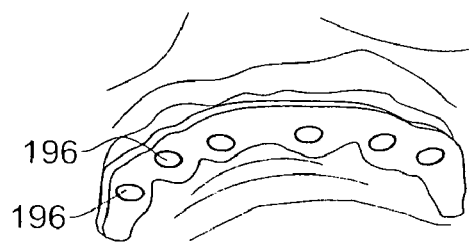
Figure 8H:
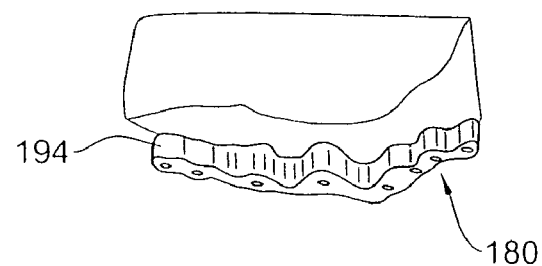
Figure 9:
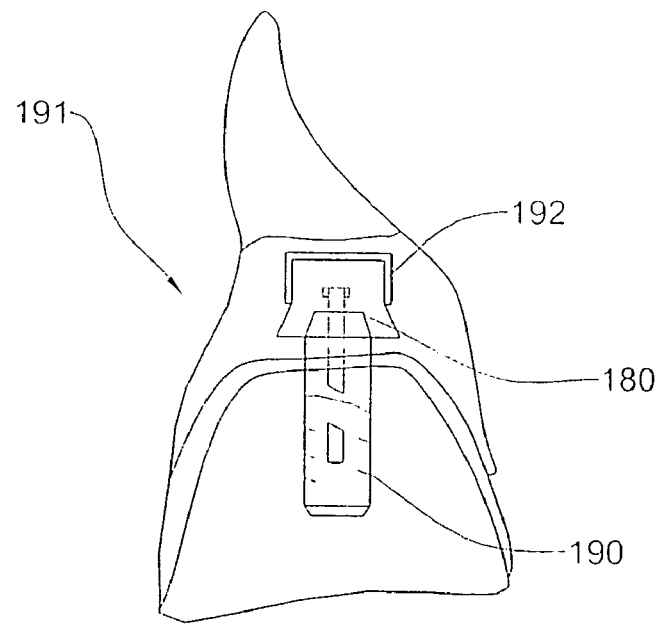
FIG. 9 is a longitudinal section illustrating how a denture is fitted on a support beam in accordance with a different embodiment of the present invention.

Further attention is now directed to FIGS. 8A through 8H and FIG. 9 illustrating a denture assembly in accordance with still a different embodiment of the present invention and a method for its manufacture. In accordance with this embodiment, an individual and personalized support beam in the form of a lower bar 180 is custom manufactured, tailored in accordance with the particular physiology of the individual. This is obtained by first preparing an imprint (model) of the individual's jaw, and then after obtaining further anatomic information, e.g. jaw structure, situation of jaw bone, etc., obtained from CT imaging (FIG. 8A), panoramic X-ray, periapical X-ray, study models, etc. implants are implanted into the imprint at the most appropriate locations and positions, in compliance with the anatomy of the individual and based on said information. Then, a second imprint is prepared which includes the precise location and position of the implants. Based on that second imprint, a computer aided manufacture system takes place (FIG. 8B) to manufacture a high accuracy lower bar 180 (FIGS. 8C-8E) formed with prepositioned bores 186 for fixedly connecting to fixtures 190 to be positioned in the individual's jaw (FIGS. 8F-8H) depending on the parameters obtained as mentioned hereinabove. Simultaneously, a denture 191 (seen in section in FIG. 10) is manufactured similar to the arrangement disclosed in FIGS. 4A and 4B, with an integrated U-sectioned super-structure 192 intended for snugly fitting over the lower bar 180. The lower bar 180 is machined into its final form as seen in FIGS. 8G and 8H formed with an upper portion 194 having a substantially rectangular cross-section. Thereafter, the lower bar 180 is fixedly attached to the fixtures 190 by means of screws 196 (position seen in FIGS. 8G and 8H) eliminating the lower bar discussed in connection with the previous embodiments.

The denture 191 is mounted on the lower bar 180 in the same fashion as disclosed in connection with the previous embodiment and as discussed for example in connection with FIG. 7A, namely substantial vertical displacement, whereby locking engagement of the denture 191 with the lower bar 180 is facilitated with a locking mechanism of any type (not seen), e.g. as disclosed in connection with the particular snap-pin lock type discussed in FIGS. 5A and 5B.

Whilst some embodiments have been described and illustrated with reference to some drawings, the artisan will appreciate that many variations are possible which do not depart from the general scope of the invention, *mutatis, mutandis*. For example, different locking mechanisms may be applied to ensure locking engagement between the denture and the support member. It is further appreciated that the hereinabove described systems and methods may be applied to the top and bottom jaw, though special care should be taken to fit an appropriate support structure to the particular anatomic parameters and features of the individual.

The invention claimed is:

1. A removable denture system comprising: a personalized support beam in a form of a lower bar adapted configured for being fixedly attached to an individual's alveolar ridge above the mucous membrane by a plurality of dental implants; a personalized denture conforming with the dental parameters of the individual and having fixedly integrated within a surface thereof a super-structure having a flat lower surface along the entire length thereof and being made of metal, said flat lower surface shaped in conformation with the lower bar; and a denture locking arrangement for articulating the denture to the lower bar preventing unintentional disengagement of the denture and allowing removal of said denture by the individual, wherein the lower surface of the super-structure bears in substantially full surface contact over the top surface of the lower bar.

2. A removable denture system according to claim 1, wherein the super structure is formed with apertures and the lower bar comprises pins adapted to be received within said apertures in the super-structure.

3. A removable denture system according to claim 1, wherein the super-structure circumferences three faces of the lower bar.

4. A removable denture system according to claim 1, wherein the super-structure has a substantially rectangular cross-section conforming with that of the lower bar, to thereby substantially eliminate any degrees of freedom therebetween.

5. A removable denture system according to claim 1, wherein the super-structure is made of a material different from that of the denture.

6. A removable denture system according to claim 5, wherein the denture is made of an acrylic material.

7. A removable denture system comprising:
a personalized support beam in a form of a lower bar fixedly attached to an individual's alveolar ridge above the mucous membrane by a plurality of dental implants; a personalized denture conforming with the dental parameters of the individual and having fixedly integrated within a surface thereof a super-structure having a flat lower surface along the entire length thereof and being made of metal, said flat lower surface shaped in conformation with the lower bar, wherein the lower surface of the super-structure bears in substantially full surface contact over the top surface of the lower bar; and
a denture locking arrangement for articulating the denture to the lower bar preventing unintentional disengagement of the denture and allowing its removal by the individual, wherein: the locking arrangement comprises one or more locking members, each disposed laterally or medially to an individual's tongue, the locking member or members comprise a housing fixed within a laterally extending bore and slidingly accommodating a locking pin axially retractable between a first position in which a head thereof is substantially flush with an inner surface of the denture and an opposite end thereof is arrested by a corresponding locking portion of the lower bar, and a second position wherein said head is extracted and the opposite end is disengaged from the locking portion of the lower bar to facilitate removal of the denture; said locking pin being snappingly arrested at respective positions of said first position and said second position.

8. A removable denture system according to claim 7, wherein the denture has an indented portion for entering a fingernail behind the head of the locking pin, to facilitate extraction of the locking pin.

9. A removable denture system according to claim 7, wherein locking studs are fixed at pre-selected retention bores formed in the lower bar, which bores are regularly used for fixedly fastening thereto a denture.

10. A removable denture system comprising: a personalized support beam in a form of a lower bar fixedly attached to an individual's alveolar ridge above the mucous membrane by a plurality of dental implants;
a personalized denture conforming with the dental parameters of the individual and having fixedly integrated within a surface thereof a super-structure being made of metal, said super-structure shaped in conformation with the lower bar and having a flat lower surface along the entire length thereof, the super-structure bears in substantially full surface contact over the top surface of the lower bar; and a denture locking arrangement for articulating the denture to the lower bar preventing unintentional disengagement of the denture and allowing removal of said denture by the individual, wherein the locking arrangement comprises: one or more locking members, each disposed laterally or medially to an individual's tongue, the locking member or members comprising a housing fixed within a laterally extending bore and slidingly accommodating a locking pin axially retractable between a first position in which a head thereof is substantially flush with an inner surface of the denture and an opposite end thereof is arrested by a corresponding locking portion of the lower bar, and a second position wherein said head is extracted and the opposite end is disengaged from the locking portion of the lower bar to facilitate removal of the denture; said locking pin being snappingly arrested at respective positions of said first position and said second position; and wherein a narrow bore is formed at the front face of the denture through which an aid may be applied to assist in retraction of the locking pin.

11. A removable denture system comprising: a personalized support beam in a form of a lower bar fixedly attached to the individual's alveolar ridge above the mucous membrane by a plurality of dental implants; a personalized denture conforming with the dental parameters of the individual and having fixedly integrated within a surface thereof a super-structure being made of metal, said super-structure shaped in conformation with at least said lower bar of the support beam and having a flat lower surface along the entire length thereof, the super-structure bearing in substantially full surface contact over the top surface of the lower bar; and a denture locking arrangement for removably though fixedly articulating the denture to the lower bar preventing unintentional disengagement of the denture.

12. A removable denture system according to claim 11, wherein the super-structure has a cross section conforming at least with an upper portion of the lower bar for snugly embracing thereof.

13. A removable denture according to claim 12, wherein the super-structure circumferences three faces of the lower bar.

14. A removable denture system according to claim 12, wherein at least an upper portion of the lower bar has a substantially rectangular cross-section.

15. A removable denture system according to claim 14, wherein the rectangular cross-section of the support beam is formed with an extracting angle in the range of 4° to 12° on one or both side faces thereof.

16. A removable denture system according to claim 14, wherein degrees of freedom between the lower bar and the denture are eliminated or substantially canceled.

17. A removable denture system according to claim 16, wherein moments of force over dental implants are substantially reduced or eliminated.

18. A removable denture system according to claim 12, wherein the super-structure has a substantially rectangular cross-section conforming with that of the lower bar, to thereby substantially eliminate any degrees of freedom therebetween.

19. A removable denture system according to claim 12, wherein an inside uppermost surface of the super-structure bears on a top ridge of the lower bar at perfect fit and tight clearance.

20. A removable denture system according to claim 12, wherein the lower bar is fixedly fitted to a leveled portion of the alveolar crest of the individual by several fixtures, with the super-structure fixedly fitted over the lower bar, with a bottom surface of the super-structure bearing flush over a top surface of the lower bar.

21. A removable denture system according to claim 11, wherein at an assembled position the locking arrangement substantially does not bear any loads.

22. A removable denture system according to claim 11, wherein the locking arrangement comprises one or more locking members, each disposed laterally or medially to the tongue.

23. A removable denture system according to claim 22, wherein the locking member is of the locking pin snap type, comprising: a housing fixed within a laterally extending bore and slidingly accommodating a locking pin axially retractable between a first position in which a head thereof is substantially flush with an inner surface of the denture and an opposite end thereof is arrested by a corresponding locking portion of a lower bar, and a second position wherein said head is extracted and the opposite end is disengaged from the locking portion of the lower bar to facilitate removal of the denture; said locking pin being snappingly arrested at respective positions of said first position and said second position.

24. A removable denture system according to claim 23, wherein the locking portion of the lower bar is a bore formed in the support beam.

25. A removable denture system according to claim 23, wherein the denture has an indented portion for entering a fingernail behind the head of the locking pin, to facilitate extraction of the locking pin.

26. A removable denture system according to claim 23, where a narrow bore is formed at the front face of the denture through which an aid may be applied to assist in retraction of the locking pins.

27. A removable denture system according to claim 11, wherein:
  a personalized lower bar is custom manufactured, tailored to meet the particular physiology of the individual;
  said lower bar is fixed to the jaw bone with a plurality of fixtures; and
  the personalized denture is removably attached over the lower bar and locked in place by the locking arrangement, such that locking members thereof directly engage the lower bar.

28. A removable denture according to claim 27, wherein the lower bar is fitted on a leveled alveolar crest of the individual.

29. A removable denture system according to claim 11, wherein the denture is fitted with a skirt extending downwards to cover at least a portion of the gums in a manner simulating and completing the gingival area.

30. A removable denture system according to claim 29, wherein the skirt extends so as to eliminate any gap extending between a lowermost end of said skirt and the individual's gum.

31. A removable denture system according to claim 11, suited for either the upper and lower jaw.

32. A removable denture system according to claim 11, wherein the denture is fitted for substantially vertical mounting over the lower bar and detaching therefrom.

33. A method for removably securing a denture to an individual, the method comprising the following steps: fixedly attaching a personalized support beam in a form of a lower bar to the individual's jaw bone; providing a denture having fixedly integrated within a surface thereof a personalized super-structure being made of metal formed with a cross-section corresponding to the lower bar, said super-structure having a flat lower surface along the entire length thereof, the super-structure bearing in full surface contact over the top surface of the lower bar, and formed with a locking mechanism comprising a pair of locking members extending at an inside face of the denture and adapted for locking engagement with a corresponding locking portion of the lower bar; and fitting the denture snugly over said lower bar and locking said denture by the locking mechanism.

34. A method according to claim 33, wherein the locking members engage with corresponding locking bores formed in the lower bar.

35. A method according to claim 33, wherein the cross-section of the lower bar has a substantially rectangular cross-section.

36. A method according to claim 33, wherein the rectangular section of the lower bar is formed with an extracting angle in the range of 4° to 12° on one or both faces thereof.

37. A method according to claim 33, wherein the super-structure has a substantially rectangular cross-section conforming with that of the lower bar, to thereby substantially eliminate any degrees of freedom therebetween.

38. A method according to claim 33, wherein the locking mechanism substantially does not bear any loads.

39. A method according to claim 33, wherein degrees of freedom between the lower bar and the denture are eliminated or substantially canceled.

40. A method according to claim 33, wherein moments of force over dental implants are substantially reduced or eliminated.

41. A method according to claim 33, wherein:
- a personalized lower bar is custom manufactured, tailored to meet the particular physiology of the individual;
- said lower bar is fixed to the jaw bone with a plurality of fixtures; and
- the personalized denture is removably attached over the lower bar and locked in place by the locking mechanism, such that locking members thereof directly engage the lower bar.

42. A method according to claim 33, suited for either the upper or lower jaw.

43. A method according to claim 33, wherein the denture is fitted for substantially vertical mounting over the support beam and detaching therefrom.

44. A method according to claim 33, wherein the denture is fitted with a skirt extending downwards to cover at least a portion of the gums in a manner simulating and completing the gingival area.

45. A method according to claim 44, wherein the skirt extends so as to eliminate any gap extending between a lowermost end of said skirt and the individual's gum.

* * * * *